United States Patent [19]

Bakke

[11] Patent Number: 4,782,212

[45] Date of Patent: Nov. 1, 1988

[54] ELECTRIC BLOOD WARMER UTILIZING A METALLIC RIBBON-FLOW CARTRIDGE

[76] Inventor: Allan P. Bakke, 609 19th Ave. SW., Rochester, Minn. 55902

[21] Appl. No.: 931,558

[22] Filed: Nov. 17, 1986

[51] Int. Cl.⁴ .......................... H05B 1/02; F24H 1/12; A61M 5/14; B67D 5/62
[52] U.S. Cl. .................................... 219/299; 128/399; 165/170; 219/302; 219/308; 219/328; 222/146.5; 604/114
[58] Field of Search ................................ 219/296–299, 219/301–305, 308, 309, 331, 328, 336, 338; 165/170; 604/113, 114; 128/399, 400; 222/146.1, 146.2, 146.5

[56] References Cited

U.S. PATENT DOCUMENTS

| 1,087,518 | 2/1914 | Wallmann | 219/336 X |
| 3,399,536 | 9/1968 | Walz | 165/170 X |
| 3,475,590 | 10/1969 | Pins | 219/302 |
| 3,485,245 | 12/1969 | Lahr et al. | 219/308 X |
| 3,492,460 | 1/1970 | Reich | 219/291 |
| 3,590,215 | 6/1971 | Anderson et al. | 219/298 |
| 3,612,059 | 10/1971 | Ersek | 128/399 |
| 4,057,918 | 11/1977 | Zeier | 219/302 X |
| 4,117,881 | 10/1978 | Williams et al. | 219/299 X |
| 4,167,663 | 9/1979 | Granzow et al. | 219/497 |
| 4,309,592 | 1/1982 | Le Boeuf | 219/299 |
| 4,314,143 | 2/1982 | Bilstad et al. | 219/497 |
| 4,358,664 | 11/1982 | Kronseder | 219/299 |
| 4,473,739 | 9/1984 | Scheiwe et al. | 219/302 |

FOREIGN PATENT DOCUMENTS

| 26/3521 | of 1927 | Australia . | |
| 15338 | 7/1929 | Australia | 219/299 |
| 2530928 | 1/1977 | Fed. Rep. of Germany | 219/296 |
| 2632985 | 1/1978 | Fed. Rep. of Germany | 219/301 |
| 2640134 | 3/1978 | Fed. Rep. of Germany | 219/299 |
| 57313 | 4/1946 | Netherlands | 165/170 |
| 90221 | 9/1937 | Sweden | 165/170 |

Primary Examiner—Anthony Bartis
Attorney, Agent, or Firm—Wayne O. Hadland

[57] ABSTRACT

An apparatus for warming flowing blood from storage to physiologic temperatures at transfusion rates up to 160 milliliters per minute includes a flat metal cartridge formed by a pair of thin generally rectangular planar members spaced slightly apart in parallelism and sealed at their peripheral edges to define a thin unobstructed, constant-width and uniform thickness ribbon-like conduit through which the blood flows from an inlet port to an outlet port at opposite ends of the cartridge. An inlet chamber and an outlet chamber, each defined by an elongated recess in one of the planar members, communicates the entire width of a corresponding end of the conduit with the inlet and outlet ports to establish uniform blood flow across the full conduit width. The cartridge is clamped between a pair of thick metal buffer blocks which dampen fluctuations in the flow of heat to the planar members of the cartridge from electric resistance heaters located on the opposite side of each buffer block.

2 Claims, 3 Drawing Sheets

ELECTRIC BLOOD WARMER UTILIZING A METALLIC RIBBON-FLOW CARTRIDGE

BACKGROUND OF THE INVENTION

The present invention generally relates to devices for heating liquids, and more particularly to a compact ribbon-flow cartridge-type blood warmer.

Blood is generally stored at a temperature near 4° C. Prior to intravenously injecting stored blood into the human body, it must be heated to near physiologic temperature (32° C. to 37° C.). During massive transfusions flow rates as high as 160 milliliters per minute may be required.

Various kinds of blood warmers presently exist. Most utilize a flexible plastic container or conduit for the blood being heated, such as plastic tubing immersed in a warm water bath or a plastic bag or pouch sandwiched between heating plates. Usually the heated flow path is quite long (in the case of tubing) or the flow is otherwise intentionally restricted (in the pouch-type heaters) to promote uniform heating of the liquid along the heated flow path.

Flexible plastic blood containers or conduits need to have substantial wall thicknesses (for example, a minimum of 0.10 mm or 4 mils is recommended for the Le Boeuf heater, U.S. Pat. No. 4,309,592) in order to prevent both rupture and, in the case of bag-type units, localized wrinkling or folding of the bag between the heating plates which would impede fluid flow. As plastic materials are good insulators but in general poor conductors of heat, the necessity of having relatively thick plastic walls imposes a requirement of large heating areas and/or fairly high heating plate temperatures in order to obtain an adequate rate of heat transfer to the blood. High heating plate temperatures impose a risk of damaging blood by overheating; large heating areas imply large priming volumes with a consequent waste of that volume of blood. Long or restricted flow paths increase the hydraulic resistance to fluid flow, thereby preventing high blood flow rates unless a high head of pressure is available; high pressure, however, tends to become self-defeating as thicker plastic walls are needed to avoid the prospect of rupture. The water bath type of blood warmers tend to underheat or overheat, depending on the rate of blood flow, and additionally are an inconvenience to have occupying space in the operating room.

Consequently a need exists for a reliable, rugged, simple and compact blood warmer, having a small priming volume and low fluid-flow resistance, that is able to warm stored blood to physiologic temperature at from low to high flow rates.

SUMMARY OF THE INVENTION

The present invention provides a ribbon-flow cartridge-type blood warmer which overcome the problems and satisfies the needs previously considered. As the blood being heated is contained in a metal cartridge, rather than a flexible plastic container, the risk of container rupture and blood spillage is eliminated. The danger of overheating blood is reduced due to the efficient heat transfer from the metal cartridge wall to the flowing blood, there being merely a very thin protectial coating of biocompatable material having relatively insignificant thermal insulating effects (due to the extreme lasting thinness of about 0.04 mil, about one percent of a flexible plastic pouch wall thickness) separating the blood from the warm metal wall surfaces. The blood enters and exits the thin wide heating channel via full-channel-width chambers at each end. The blood being heated hence uniformly flows as a thin wide ribbon between the warm cartridge walls, presenting a large surface area yet occupying a small (about 10 milliliters) priming volume, while flowing directly and efficiently from inlet to outlet over a short heated path.

In an experiment using water with a 74 inch pressure head in a Fenwal brand of blood administration set (Fenwal Laboratories is a division of Baxter Travenol Laboratories, Inc., which is the assignee of U.S. Pat. Nos. 4,167,663 and 4,314,143), the free flow through the set (which included a Fenwal brand warmer) was about 150 milliliters per minute. With no warmer in the circuit, free flow (not through the infusion set alone) was about 400 milliliters per minute. When a prototype ribbon-flow warmer was substituted in place of the standard Fenwal brand warmer, free flow was still about 400 milliliters per minute, showing that the instant device had negligible flow resistance compared to the infusion set itself. As a measure of thermal performance, the prototype was able to warm ice water to 33° C. at a flow rate of 160 milliliters per minute, while maintaining a temperature of only 37° C. on the metal buffer block (measured close to the cartridge, near the outlet).

Accordingly, the present invention relates to an apparatus for warming blood, and consists primarily of a hollow flat metal container called a cartridge in which blood is warmed as it passes through, the cartridge being clamped between two thick metal plates having good thermal conductivity called buffer blocks. The buffer blocks provide a large thermal inertia to dampen fluctuations in the flow of heat to the flat metal walls of the cartridge from heating means located on the opposite side of each buffer block. Means for controlling the heating to keep the buffer blocks in a desired temperature range are also provided.

DESCRIPTION OF THE PREFERRED EMBODIMENT

Figure 1:
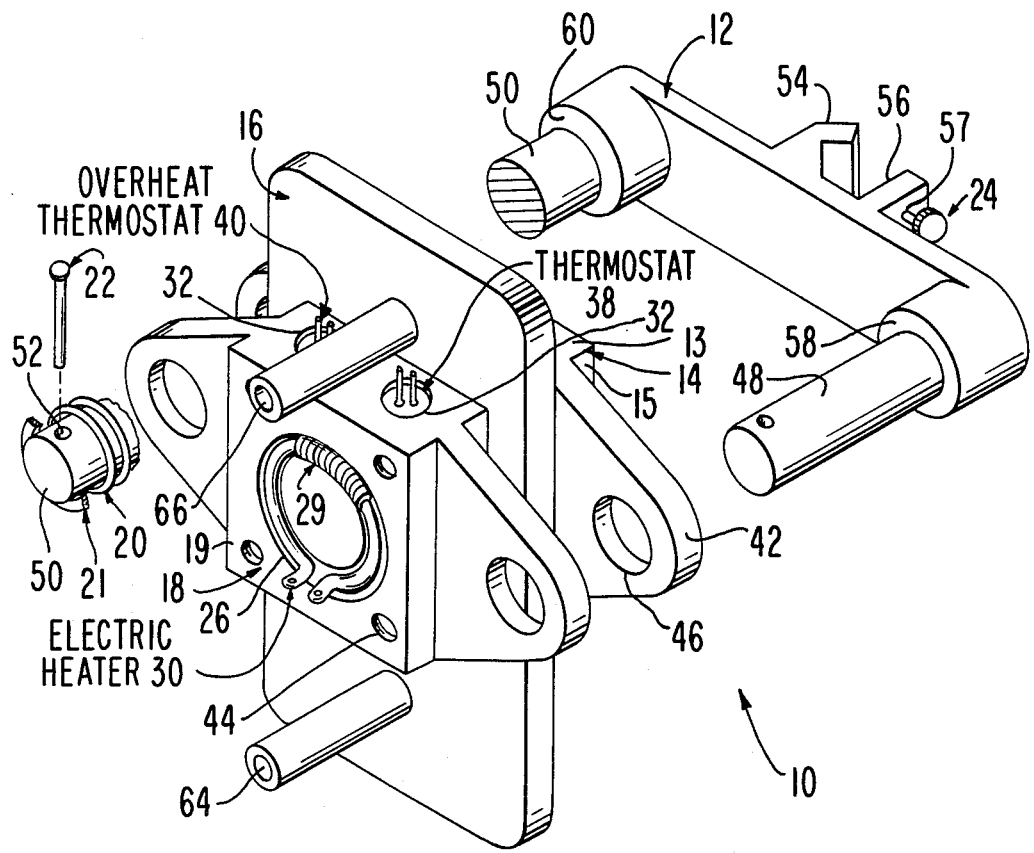
FIG. 1 is a partially-exploded view of the preferred embodiment of the present invention, a ribbon-flow cartridge-type blood warmer, shown with the front and back buffer-block cover assembly 79, shown in FIG. 5, removed. The far-side shaft is shown broken, with the broken-off portion shown as having passed through and stopped in front of the near buffer block far ear.
Figure 5:
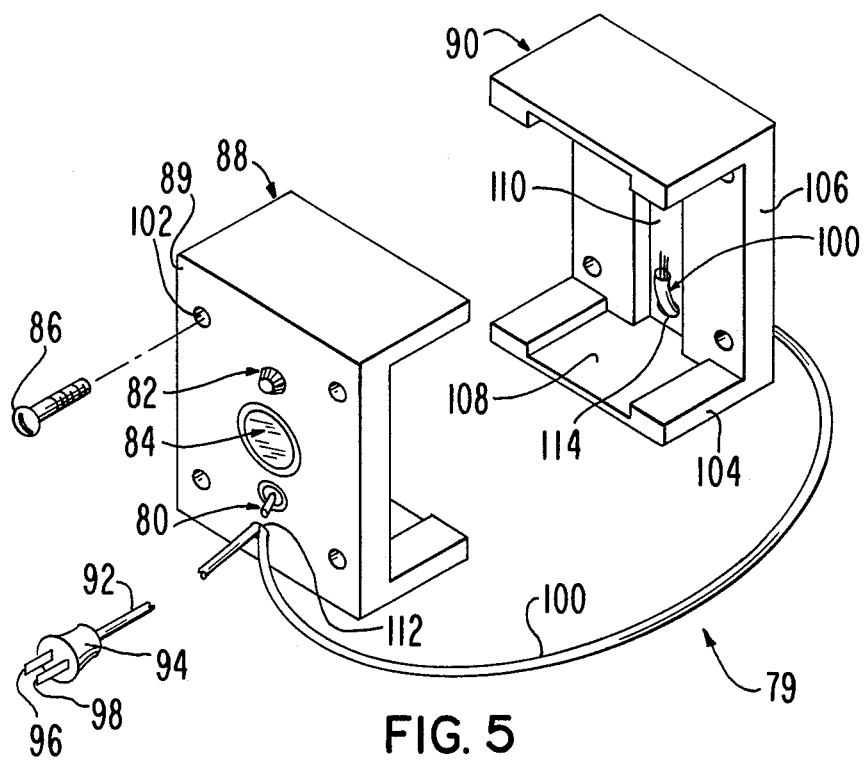
FIG. 5 is a perspective view of the front and back buffer-block cover assembly, which fits over the buffer-blocks (14 and 18) shown in FIG. 1 to form the complete assembly of the blood warmer.

Referring now to the drawings, and more particularly to FIG. 1, there is shown a ribbon-flow cartridge-type blood warmer, generally designated 10, which in combination with a front and back cover assembly 79 shown in FIG. 5 comprises the preferred embodiment of the present invention. The apparatus 10 includes a base 12 which directly supports both a first buffer-block 14 and a second buffer-block 18 by two round shaft extensions 48 and 50, which pass through holes 46 in ears 42 protruding from each side 15 of said blocks 14 and 18. A blood-containing cartridge 16 is clamped between and supported by said buffer-blocks 14 and 18. Blood inlet pipe 64 and outlet pipe 66 protrude from said cartridge below and above said second buffer-block 18. A coil spring 20 and a round flat washer 21 (shown broken away) fit over each shaft 48 and 50; two retaining pins 22, one inserted through each shaft end hole 52, secure the aforementioned assemblage of elements together. Each cover 88 and 90 (see FIG. 5) of said cover assembly 79 is attached to each corresponding buffer-block 18 and 14 by four screws 86 which pass through clearance holes 102 in each cover 88 and 90, and screw into tapped blind holes 44 in each buffer-block 18 and 14.

The base 12 is shown in FIG. 1 in a perspective view; it can be made from any suitable material (e.g., cast iron, steel, or aluminum) and can be fabricated by casting or by machining from a solid block of material. An angled lug 54, and a straight lug 56 having a tapped through-hole 57 in which a thumbscrew 24 is inserted, protrude from the back of base 12 thereby providing a means for attaching the base 12 to the kind of vertical-rob support stands commonly found in medical facilitites. Two round shafts 48 and 50 extend horizontally from corresponding bosses 58 and 60 on the front of base 12, thereby providing a means for directly supporting the first buffer-block 14 and the second buffer-block 18. A spring 20 and a flat round washer 21 are slipped over the end of each shaft 48 and 50, and are locked in place by two retaining pins 22, one being inserted through each hole 52 in the extreme end of each shaft 48 and 50. The two springs 20 thereby provide a clamping means, pressing the second buffer-block 18 against the cartridge 16, which in turn bears against the first buffer-block 14 which is reacted by the two bosses 58 and 60 of base 12.

A first buffer block 14 and an identical second buffer block 18 (each having two ears 42 with holes 46) fit freely over the shafts 48 and 50 of base 12, clamping cartridge 16 between said blocks. The surface of each buffer-block 14 and 18 which contacts the cartridge 16 is flat and smooth; the face 19 on the opposite side of each block has one blind tapped hole 44 near each of the four corners, and a centered shallow annular groove 26 for accepting a circular electrical resistance type of heating means. In the prototype apparatus two 600 watt circular CalRod type of electric heaters 28 and 30 were used, one in each buffer-block 14 and 18. A rope 29 of high temperature insulating material (such as asbestos) is placed over each electric heater 28 and 30 to prevent direct contact with the covers 90 and 88. Two shallow round holes in the top surface 13 of each buffer-block 14 and 18, located close to the cartridge-containing surface, form wells 32 for two thermostats. One normal operating thermostat (34 for block 14, 38 for block 18), and one safety over-heat themostat (36 for block 14, 40 for block 18), are inserted into the wells 32 in each block. In the prototype the buffer-blocks 14 and 18 were made of aluminum, and (excluding the ears 42) were 2.54 cm thick by 12.7 cm square.

Figure 2:
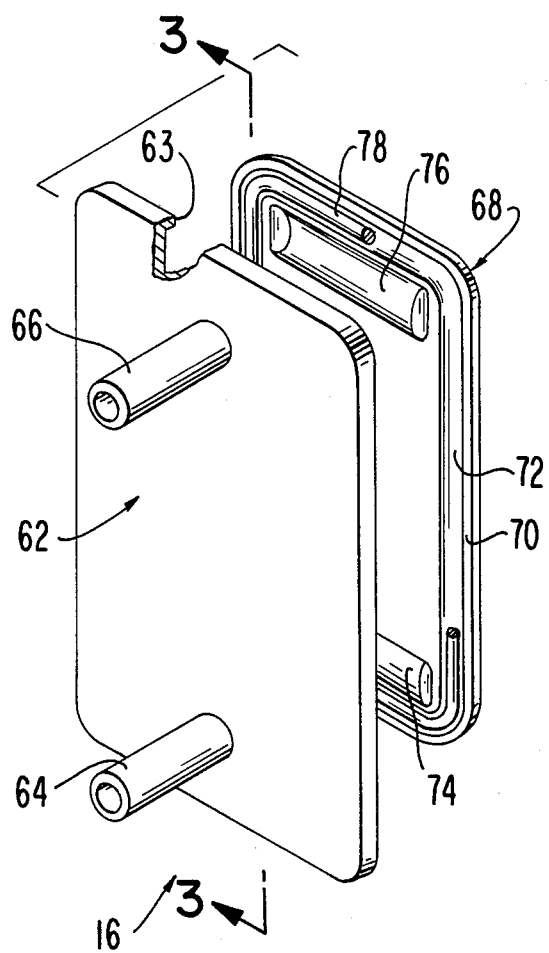
FIG. 2 is an exploded view of the blood-containing cartridge.
Figure 3:
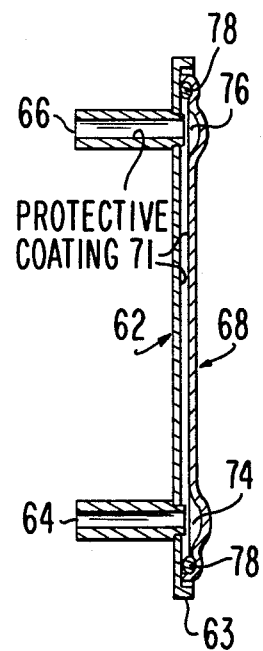
FIG. 3 is a non-exploded sectional view through the cartridge taken along the vertical centerline 3—3 shown in FIG. 2.
Figure 4:
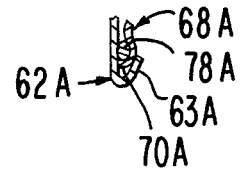
FIG. 4 shows an alternative non-separable formed edge design (as compared to the separable edge design as shown in the preceding FIG. 3).

The blood-containing cartridge 16 is shown in FIG. 2 in an exploded view; FIG. 3 is a non-exploded transverse sectional view through the center of cartridge 16. The cartridge is made up of two major components, a front or outer plate 62 and a back or inner plate 68. A blood inlet pipe 64 and a blood outlet pipe 66 are permanently attached to outer plate 62; FIG. 3 shows said pipes as being simply pressed into through-holes in said plate, thereby forming inlet and outlet ports for blood to enter and leave the interior of the cartridge. The periphery of outer plate 62 is turned up to form a lip 63 that ensures proper alignment with inner plate 68. The periphery of inner plate 68 is turned up to form a rim 70, which fixes the distance between the opposed inner surfaces of plates 62 and 68 when they are pressed together as shown in FIG. 3; a gap distance of about 0.8 mm was used for the prototype apparatus. A groove 72 is formed just within the rim 70 of inner plate 68 to receive a perimeter seal 78 (shown broken away). Two horizontal trough-shaped recesses forming chambers 74 and 76, located just inboard of the perimeter seal groove 72 and opposite inlet and outlet pipes 64 and 66, are formed into and run across the bottom and top of the inner plate 68. For the prototype apparatus the cartridge 16 outer plate 62 and inner plate 68 were made of approximately 0.8 mm (i.e., 30 mils) thick sheet aluminum; the inlet 64 and outlet 66 pipes were also made of aluminum. Other materials that have very good thermal conductivity and are easily formed, such as alloys of copper, could also be used. The wetted interior surfaces of the plates 62 and 68 (which includes the interior surfaces of pipes 64 and 66) are coated with a very thin protective coating 71 of biocompatible material, such as a one micron (0.04 mil) thick coating of Union Carbide Corporation's Type C parylene (polymonochloro-para-xylylene) thermoplastic polymer coating. The perimeter seal 78 is made from a resilient biocompatible elastomer such as silicone rubber. All materials used for components of the cartridge 16 must be able to withstand the temperatures reached in the steam-sterilization autoclaving process. The embodiment of the cartridge shown in FIGS. 2 and 3 has separable inner and outer plates 68 and 62, that can be taken apart, cleaned and sterilized, and reused. The cartridge may also be made in a disposable inseparable version by simply crimping the lip 63A of the outer plate 62A over the rim 70A of the inner plate 68A; this construction detail is shown in FIG. 4.

The buffer-block cover assembly 79, shown in FIG. 5, is comprised of two channel-shaped covers 88 and 90, connected together by an electrical connecting cord 100 passing through a hole 112 in front cover 88 and a similar hole 114 in back cover 90. An electrical power cord 92 having a plug 94 with a first terminal 96 and a second terminal 98 also passes through hole 112 in the front cover 88. Each channel-shaped cover 88 and 90 has a central vertical web 106, connected to horizontal flanges 104 at the top and at the bottom of said web. The cover flanges 104 are slightly shorter than the full thickness of the buffer-blocks 14 and 18, whereby ensuring that said buffer-blocks will contact the cartridge 16 without interference. Central recesses 110 and 108 are provided in the web 106 and flanges 104 of each cover to accommodate electrical wiring. Each cover is a one-piece unit, made from an electrically insulating and heat-resistant material such as Bakelite thermo-setting plastic. The web 106 and flange 104 portions of each cover fit over the corresponding faces 19 and top and bottom surfaces of each buffer-block 14 and 18, keeping the electric heaters 28 and 30 in position and providing protection for interconnecting wiring and for thermostats 34, 36, 38, and 40. An on-off switch 80, a fuse 82, and an indicating light 84 are mounted on the face 89 of the front cover 88.

Figure 6:
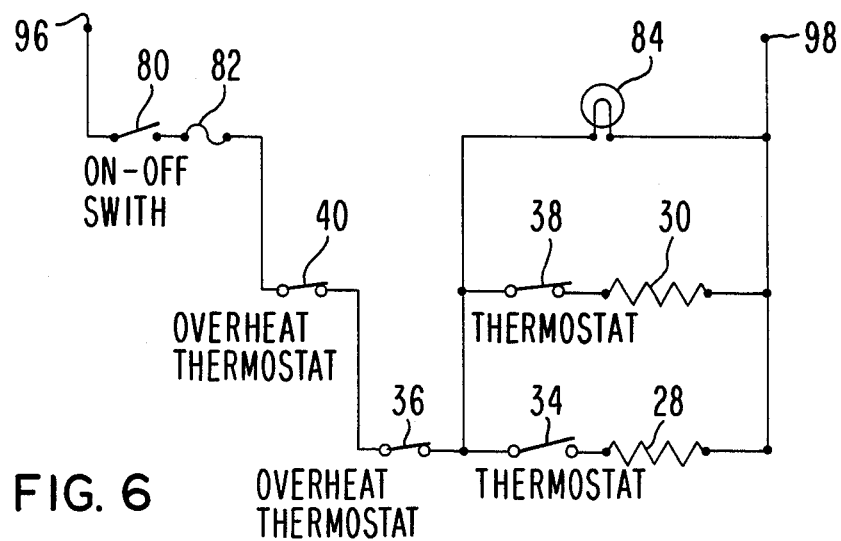
FIG. 6 is a schematic diagram of the electrical elements, showing those which are mounted on the front cover (top horizontal line), mounted on the second (front) buffer block (middle horizontal line), and mounted on the first (back) buffer-block (bottom horizontal line).

FIG. 6 is a schematic diagram showing how the electrical components are connected together. The on-off switch 80, the fuse 82, and the indicating light 84 (all mounted on the front cover 88) are shown on the top horizontal line of the schematic diagram. The middle horizontal line of the diagram shows the devices mounted on second buffer-block 18; the bottom horizontal line shows the devices mounted on first buffer-block 14. All four buffer-block-mounted thermostats 34, 38, 36, and 40, are single-pole single-throw open-on-rising-temperature hermetically sealed snap-action devices, such as those made by Texas Instruments (Klixon brand) and by Elmwood Sensors Inc. thermostats 34, 38, 36, and 40, should be closed below approximately 36° C. The two normal operating thermostats 34 and 38 should be open above approximately 40° C. The overheat safety protection thermostats 36 and 40 are set to open at a slightly higher temperature, e.g. 1° C. higher, than the normal operating thermostats 34 and 38. When a voltage is applied across the terminals 96 and 98 (110 volts AC was used for the prototype device) and the on-off switch 80 is closed (power turned on), the light 84 glows and the two thermostats 34 and 38 each independently cycle on and off to keep the buffer-blocks 14 and 18 in the desired temperature range, e.g. between 36° C. and 40° C. If a normal operating thermostats 34 or 38 should fail closed, the associated over-temperature thermostat 36 or 40 would then open, cutting off power to both heating elements 28 and 30 and also to the light 84, thereby indicating a malfunction.

In operation, cool blood under slight pressure enters the cartridge 16 at inlet pipe 64 via such means as a flexible tube slipped over said pipe. The flow spreads into inlet chamber 74, and then moves as a thin wide ribbon through the heated shallow passage between outer plate 62 and inner plate 68 until it enters outlet chamber 76, from whence the warmed blood exits the cartridge at outlet pipe 66.

From the foregoing description, it will be apparent that the invention disclosed the herein provides a novel and advantageous blood warmer design. As will be understood by those familiar with the art, the invention may be embodied in other specific forms without departing from the spirit or essential characteristics thereof. For example, more complex temperature sensing and heating control means (such as an electronic system using proportional control, with triac circuitry and zero-point switching) could be used in place of the less complex arrangement shown in FIG. 6. The form hereinbefore described is merely a preferred or exemplary embodiment of the invention.

I claim:

1. An apparatus for warming blood for transfusion, comprising:
   a fluid-impervious rigid flat metal cartridge defining an enclosed cavity of small volume, having an inlet port and an outlet port at opposite ends thereof, the interior of said cartridge being compatible with the temporary storge of blood;
   said cartridge including a pair of thin metal generally rectangular planar members spaced slightly apart and in parallelism with each other, said members being sealed together at their edges to define an unobstructed constant-width and uniform-thickness thin ribbon-like conduit for fluid between the interior surfaces of said members;
   said cartridge further including an elongated recess defining an inlet chamber communicating with said inlet port, and an elongated recess defining an outlet chamber communicating with said outlet port, each chamber running completely across and communicating with a corresponding end of said conduit, whereby fluid can uniformly flow into and out of said thin ribbon-like conduit across the full conduit width;
   two thick buffer blocks made of metal having good thermal conductivity, each having a flat clamping surface disposed to clamp against a corresponding flat outer surface of said cartridge, and each having on the side opposite of said flat clamping surface a heatable surface disposed to accommodate a heating means;
   means for supporting said buffer blocks opposite one another with each said clamping surface facing toward and parallel to the other;
   means releasably clamping said cartridge between and against said supported buffer blocks;
   means for heating each buffer block heatable surface;
   temperature sensing means located closely adjacent to said cartridge on each buffer block for sensing the temperature of each buffer block; and
   control means responsive to said temperature sensing means to control the amount of heat supplied by said heating means to each buffer block.

2. An apparatus for warming blood for transfusion, comprising:
   a fluid-impervious rigid flat metal cartridge defining an enclosed cavity of small volume, having an inlet port and an outlet part at opposite ends thereof, the interior of said cartridge being compatible with the temporary storage of blood, the exterior of said cartridge having two flat heatable surfaces;
   said cartridge including a pair of thin metal generally rectangular planar members spaced slightly apart and in parallelism with each other, said members being sealed together at their edges to define an unobstructed constant-width and uniform-thickness thin ribbon-like conduit for fluid between the interior surfaces of said members;
   said cartridge further including an elongated recess defining an inlet chamber communicating with said inlet port, and an elongated recess defining an outlet chamber communicating with said outlet port, each chamber running completely across and communication with a corresponding end of said conduit, whereby fluid can uniformly flow into and out of said thin ribbon-like conduit across the full conduit width;
   means for heating each of said cartridge heatable surfaces;
   temperature sensing means for sensing the temperature of said cartridge; and
   control means responsive to said temperature sensing means to control the amount of heat supplied by said heating means to each cartridge flat side.

* * * * *

UNITED STATES PATENT AND TRADEMARK OFFICE
CERTIFICATE OF CORRECTION

PATENT NO. : 4,782,212

DATED : Nov. 1, 1988

INVENTOR(S) : Allan P. Bakke

It is certified that error appears in the above-identified patent and that said Letters Patent is hereby corrected as shown below:

```
Col. 1, line 57, change "overcome" to --overcomes--.
Col. 1, line 64, change "protectial" to --protective--.
Col. 1, line 67, change "lasting" to --coating--.
Col. 2, line 17, change "not" to --now--.
Col. 3, line 35, change "vertical-rob" to --vertical-rod--.
Col. 3, line 66, change "cartridge-containing"
                to --cartridge-contacting--.
Col. 4, line 65, change "whereby" to --thereby--.
Col. 5, line 24, after "Inc." insert --All--.
Col. 5, line 24, after "thermostats" insert --,--.
Col. 5, line 37, change "thermostats" to --thermostat--.
Col. 5, line 51, change "disclosed the herein"
                to --disclosed herein--.
Claim 2,
Column 6, line 56, change "communication"
                   to --communicating--.
```

Signed and Sealed this

Twenty-eighth Day of November 1989

Attest:

JEFFREY M. SAMUELS

Attesting Officer    Acting Commissioner of Patents and Trademarks